United States Patent [19]

Coutré et al.

[11] Patent Number: 5,127,907
[45] Date of Patent: Jul. 7, 1992

[54] SYSTEM FOR ELIMINATING OR REDUCING STATIC ELECTRICITY IN INFUSION PUMPING SYSTEMS

[75] Inventors: James E. Coutré, Concord; Scott F. Jenney, North Reading, both of Mass.

[73] Assignee: Abbott Laboratories, Abbott Park, Ill.

[21] Appl. No.: 623,200

[22] Filed: Dec. 6, 1990

[51] Int. Cl.$^5$ .............................................. A61M 5/20
[52] U.S. Cl. .................................. 604/151; 361/212; 604/218
[58] Field of Search ................. 604/218, 151; 361/212, 361/220

[56] References Cited

U.S. PATENT DOCUMENTS

| | | | |
|---|---|---|---|
| 4,475,141 | 10/1984 | Antonevich | 361/212 |
| 4,577,256 | 3/1986 | Breidegam | 361/212 |
| 4,585,320 | 4/1986 | Altavela et al. | 361/212 |
| 4,627,840 | 12/1986 | Cuadra et al. | 604/181 |
| 4,696,671 | 9/1987 | Epstein et al. | 604/67 |
| 4,731,068 | 3/1988 | Hesse | 604/218 |
| 4,744,955 | 5/1988 | Shapiro | 604/218 |
| 4,866,565 | 9/1989 | Wray, Jr. | 361/220 |

Primary Examiner—Paul J. Hirsch
Attorney, Agent, or Firm—Weingarten, Schurgin, Gagnebin & Hayes

[57] ABSTRACT

A system for eliminating or reducing static electricity in infusion pumping systems which may cause artifacts in electrocardiograms is disclosed. Infusion pumping systems deliver prescribed infusates to a patient. Frequently, such infusion systems are used in conjunction with electrocardiogram monitors. Static electricity generated at or by the infusion pumping system may cause artifacts in the electrocardiogram monitor. The present invention reduces or eliminates this static electricity by forming parts in relative motion of a similar material to reduce generation of static electric charges. The pumping piston and diaphragm wall of a pumping chamber may be formed from a similar material. The valve pistons and valve diaphragms may be formed of a similar material. The removable pumping cassette and cassette receiver may be formed from a similar material. The present invention also reduces the formation of static electric charges by coating the cassette with an antistatic material. In a further embodiment of the present invention, the fluid flow line may include an electrical conductor connected to a ground.

31 Claims, 4 Drawing Sheets

SYSTEM FOR ELIMINATING OR REDUCING STATIC ELECTRICITY IN INFUSION PUMPING SYSTEMS

FIELD OF THE INVENTION

This invention relates to the field of infusion therapy for a patient and more particularly to a novel infusion pumping system able to reduce or eliminate artifacts in an electrocardiogram of a patient caused by static electricity.

BACKGROUND OF THE INVENTION

Intravenous infusion therapy is prescribed where it is desirable to administer medications and other fluids directly into the circulatory system of a patient. Infusion pumping systems are used to pump the prescribed infusates from a bag, bottle, or syringe to the patient. For example, the infusion system of Epstein, U.S. Pat. No. 4,696,671, provides a computer-controlled infusion system using a disposable cassette and able to pump plural fluids through plural input ports and at least one patient output port simultaneously or in time sequence.

For many patients, an infusion pumping system is frequently used in conjunction with an electrocardiograph to monitor the heartbeats of the patient. The electrocardiogram (ECG) obtained comprises a number of leads, or records of potential differences, between electrodes positioned on the surface of the patient's body. Typically, a four-lead system is used to monitor the patient's condition. A twelve-lead system is used to obtain a more accurate ECG on which to base diagnoses and therapeutic prescriptions.

The ECG is a record of the electrical signals of the patient's heartbeats. An artifact in this record is undesirable because, if not detected and identified as an artifact, it may cause a physician to misinterpret the ECG. The strongest portion of the ECG is known as QRS and is the most important portion of the signal for interpreting the patient's condition. All ECG monitors filter out artifacts to some extent, and ideally the artifact will be too low to be confused with QRS. The twelve lead ECG monitors have a better capacity for filtering out artifacts of all sorts than the four-lead monitors. However, the potential for artifact occurrence still exists in all ECG systems.

Artifacts may be caused by a number of phenomena: room lights, patient movement, perspiration on the patient's skin. Artifacts have also been observed as associated with infusion pumping systems. Previously, it had been thought that pump-induced artifact was due to a piezoelectric effect of a changing strain rate in the plastic tubing inducing a miniscule electric current. It had been thought that all infusion pumps exhibited this effect, but little or no work on reducing or eliminating the effect had been accomplished.

SUMMARY OF THE INVENTION

The present inventors have discovered that artifact induced by infusion pumping systems is not caused primarily by a piezoelectric effect. Rather, artifact is caused by static electricity. Accordingly, the inventors have discovered that reducing or eliminating the static electricity generated at or by the pumping system significantly reduces the occurrence of artifact in the ECG.

In a high static environment, static electricity in the pumping system has two major contributors: walking by or handling the pumping system tubing and the pumping itself. Regarding the pumping itself, the present work showed that artifacts occurred primarily on the fill stroke of the pump cycle and when ionic solutions were being pumped. The fill stroke is the most rapid stroke of the cycle; the pumping chamber is filled with fluid quickly, while the fluid is delivered to the patient more slowly. In the prior art pumping systems, the pumping piston is metal and the diaphragm is silicon rubber. Accordingly, in a high static environment and particularly during rapid relative motion between the piston and the diaphragm, charges were generated on the piston and diaphragm. The charges then were carried away to the patient in the ionic solution. Applicants found that charges could be generated in other ways as well. For example, sliding the cassette into the pumping system housing also brought dissimilar materials into contact and generated charges.

In the present invention, the pumping piston face which contacts the diaphragm of the pumping chamber and the diaphragm are made with a similar material. The valve pistons and valve diaphragms may also be made with a similar material. Similarly, the cassette and those portions of the housing in contact with the cassette may be formed of a similar material. Also, a ground wire may be embedded in the cassette along the fluid flow path to carry any charges to ground rather than to the patient, or the cassette may be coated with an antistatic material.

DESCRIPTION OF THE DRAWINGS

The invention will be more fully understood from the following detailed description taken in conjunction with the accompanying drawings in which.

DETAILED DESCRIPTION OF THE INVENTION

Figure 1:
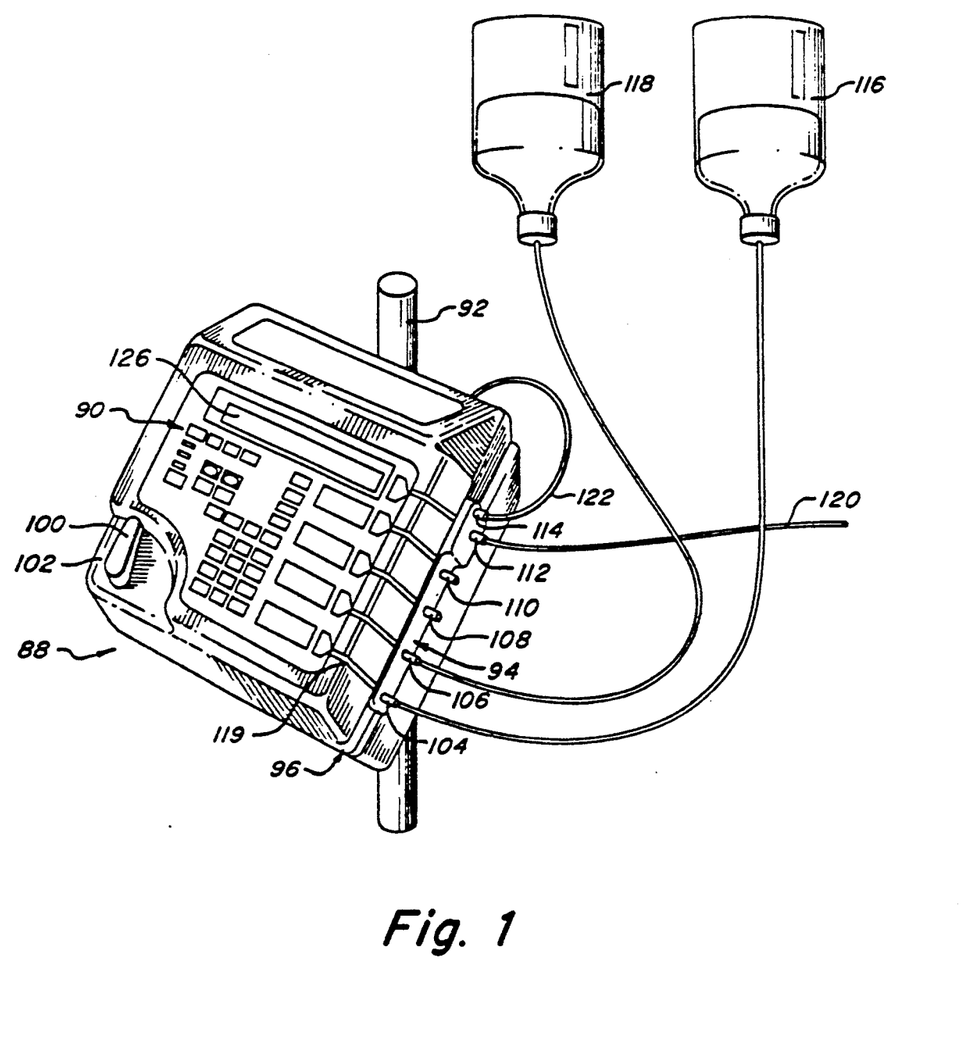
FIG. 1 is an isometric view of a housing and control panel for an infusion system having a removable cassette and plural fluid input ports and at least one patient output port.

An infusion pumping system is shown generally at 88 in FIG. 1. This infusion pumping system is substantially as described in U.S. Pat. No. 4,696,671, the disclosure of which is incorporated herein by reference. This infusion system has plural fluid input ports and at least one patient output port and uses a removable, disposable cassette.

A housing 88 is mounted to a conventional IV pole 92 such that its front panel generally designated 90 is oriented at an angle selected to provide ease of operator access, preferably 45°. A disposable cassette generally designated 94 to be described is slideably mounted in a channel generally designated 96 provided therefor on one side of the housing 88. The cassette 94 is oriented at the same angle of inclination to the vertical to allow both pumping with slight quantities of air in the fluid flow path and the expeditious removal of air from the fluid flow path. A locking lever 100 having a safety mechanism 102 to be described is provided to removably retain the cassette 94 in the channel 96 on the side of the housing 88. The cassette 94 includes four fluid input ports 104, 106, 108, and 110, a patient output port 112, and a vent output port 114. A plurality of fluid containers are positioned a predetermined vertical distance above the housing 88 and directly connected to corresponding ones of the fluid input ports, two such fluid containers 116, 118 connected to the input ports 104, 106 being specifically illustrated. It will be appreciated that two additional fluid containers, bags, or syringes, not shown, may be directly connected to the ports 108, 110. A plurality of indicating lines 119 are provided on the side of the housing. A patient output line 120 is connected to the output port 112, and a collection bag line 122 is connected between the vent output port 114 and a collection bag removably retained on the back of the housing 88, not shown.

The front panel 90 includes an operator-interactive display 126 and a plurality of command keys for operator control of the infusion system. By pressing the appropriate keys, the operator programs the infusion system with data such as the rate, volume, and time of infusions on each of up to four input lines.

Figure 2A:
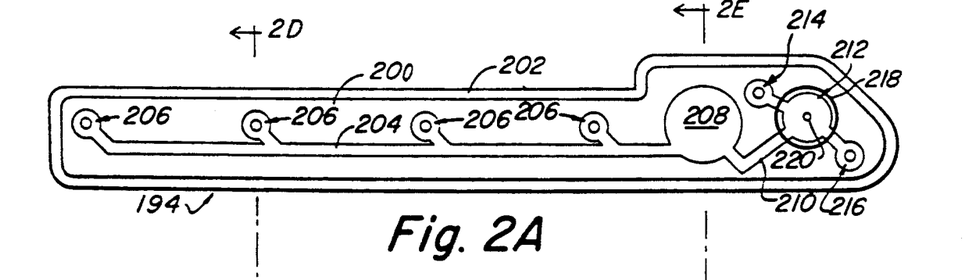
FIG. 2A is a plan view illustrating one portion of a cassette of the infusion system of FIG. 1.
Figure 2B:
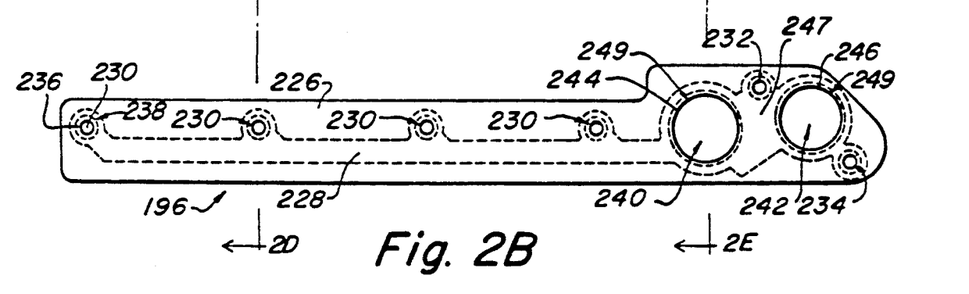
FIG. 2B is a plan view illustrating another portion of the cassette of the infusion system of FIG. 1.
Figure 2C:
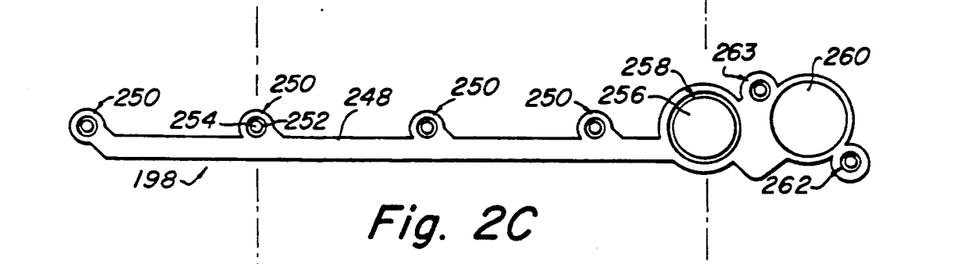
FIG. 2C is a plan view illustrating a flexible diaphragm of the cassette of the infusion system of FIG. 1.

Referring now to FIG. 2 generally illustrated at 194 in FIG. 2A is a first housing portion, generally designated at 196 in FIG. 2B is a second housing portion, and generally designated at 198 in FIG. 2C is a flexible diaphragm of a disposable cassette of the infusion system having plural fluid input ports and at least one patient output port. As shown in FIG. 2A the housing portion 194 includes an injection molded clear plastic member 200 that meets appropriate U.S. Pharmacopia standards. The member 200 includes an integral upstanding peripheral flange 202 and a longitudinally extending fluid flow channel 204. A plurality of longitudinally spaced fluid input apertures generally designated 206 and a pumping chamber generally designated 208 are integrally formed with the member 200 in communication with the fluid flow path channel 204. A channel 210 is integrally formed with the plastic material 200 between the pumping chamber 208 and a pressure chamber generally designed 212. The chamber 212 is integrally formed with the plastic material 200. A patient output aperture generally designated 214 and a vent output aperture generally designated 216 are integrally formed with the plastic material 200 and are in fluid communication with the pressure chamber 212. A disc 218 having a central aperture 220 is provided over the pressure chamber 212 that cooperates with the walls defining the pressure chamber to prevent the collapse of the diaphragm 198 (FIG. 2C) into the chamber 212. As best seen in FIG. 2D, the cassette housing portion 194 includes an annulus 222 defining an input fluid port integrally formed surrounding a corresponding one of the fluid apertures 206, 214, 216 (FIG. 2A). Diametrically opposed locking flanges 224 are integrally formed on the ends of each annulus 222. The plastic member 200 includes longitudinally extending shoulders 225 that abut longitudinally extending guides provided therefor on the side of the housing 88 (FIG. 1) that prevents the movement of the cassette 94 (FIG. 1) in a direction transverse to its plan.

Referring now to FIG. 2B the housing portion 196 includes a clear plastic member 226 that mates in fluid tight sealing engagement with the housing portion 194 (FIG. 2A). The member 226 includes a longitudinally extending diaphragm receiving recess 228. A plurality of longitudinally spaced input valve plunger receiving apertures generally designated 230 are provided through the plastic member 226. An output valve plunger receiving aperture 232 is provided in the plastic member 226 and a vent valve plunger receiving aperture 234 is provided in the plastic member 226. An upstanding annular flange 236 integrally formed with the plastic member 226 is provided surrounding each of the input valve plunger receiving apertures 230, the vent valve plunger receiving aperture 234, and the output valve plunger receiving aperture 232. A semicircular channel portion generally designated 238 integrally formed in the plastic member 226 is provided surrounding each of the annular flanges 236 that are in communication with the channel 228. The plastic member 226 of the housing portion 196 includes a pumping piston receiving aperture generally designated 240 and a pressure transducer receiving aperture generally designated 242. An annular flange 244 integrally formed in the plastic member 226 in communication with the channel 228 is provided surrounding the aperture 240, and an annular flange 246 integrally formed in the plastic member 226 is provided surrounding the aperture 242. Semicircular channel portions generally designated 249 are also provided around the annular flanges 244, 246. A recess 247 is provided intermediate the flanges 244, 246 forming a continuation of recess 228. The ends of the flanges 236, 244, 246 are flush with the generally planar surface of the plastic member 226.

Referring now to FIG. 2C, the diaphragm 198 is preferably an injection molded length of silicone rubber that meets the appropriate U.S. Pharmacopia standards. The diaphragm 198 includes a longitudinally extending reinforced seal portion 248 having a transverse width greater than the transverse width of the longitudinally extending fluid channel 204 (FIG. 2A) that is received in the recess 228 (FIG. 2B). A plurality of longitudinally spaced input fluid valve pads generally designated 250 are provided on the longitudinally extending reinforced seal portion 248. Individual ones of the valve pads 250 are aligned with corresponding ones of the apertures 206 (FIG. 2A) and apertures 230 (FIG. 2B). The valve pads 250 include an annular recess 252 that is individually aligned with a corresponding one of the annular flanges 236 (FIG. 2B) and an integral upstanding cylindrical projection 254 that are individually aligned with corresponding ones of the apertures 206 (FIG. 2A) and apertures 238 (FIG. 2B).

A convex dome 256 surrounded by an annular recess generally designated 258 is provided on the diaphragm 198. The recess 258 is aligned with the annular flange 244 (FIG. 2B) and the dome 256 is aligned with the aperture 240 (FIG. 2B) and the pumping chamber 208 (FIG. 2A). A thin circular portion 260 is provided on the diaphragm 198. The portion 260 is aligned with the flange 246 (FIG. 2B) and the pressure chamber 218 (FIG. 2A) A vent valve pad generally designated 262 is provided on the diaphragm 198 adjacent the member 260 in alignment with the apertures 216 (FIG. 2A), 234 (FIG. 2B), and a patient output valve pad generally designated 263 is provided adjacent the cylindrical depression 258 in alignment with the apertures 214 (FIG. 2A), 232 (FIG. 2B). Each of the pads 262, 263 include an integral upstanding cylindrical projection surrounded by an annular recess like those described above for the pads 250. The cylindrical projections of the valve pads 250, 262, 263 have dimensions larger than the dimensions of the corresponding aligned apertures of the member 194 to provide a seal thereagainst to prevent fluid flow. The thickness of the portions 248, 256 (FIG. 2C) is selected to provide a stiffness sufficient to prevent their unintended collapse into the portions 204, 208 (FIG. 2A) during operation.

Figure 2D:
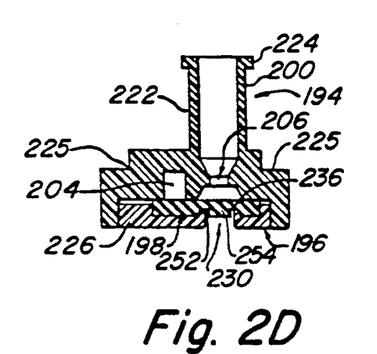
FIG. 2D and 2E are sectional views of the cassette taken along the lines D—D and E—E of FIGS. 2A-2C of the infusion system of FIG. 1.
Figure 2E:
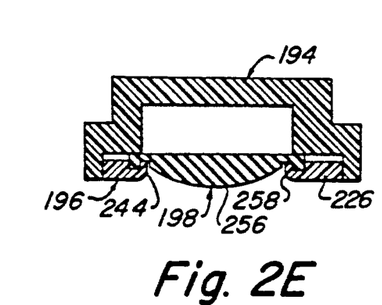

In the assembled condition of the disposable cassette as best seen in FIGS. 2D and 2E, the diaphragm 198 is sandwiched between the housing portion 194 and the housing portion 196. The longitudinally extending seal portion 248 of the diaphragm 198 is received in the diaphragm receiving recess 228, the solid cylindrical projections 254 of the valve pads 250, 262, 263 extend into corresponding ones of the apertures 230, 232, 234, the dome portion 256 is received over the mouth of the pumping chamber 208, and the member 260 is received over the disc 218 and pressure chamber 212. Any suitable means such as ultrasonic welding may be employed to secure the two housing portions together in fluid tight sealing engagement. The cassette is oriented in use preferably at 45° to the vertical as described above in connection with the description of FIG. 1. As will readily be appreciated, any air in the fluid flow channel 204 (FIG. 2A) rises upward therealong through the pumping chamber 208 (FIG. 2A) and fluid path 210 into the pressure chamber 212 (FIG. 2A). The system controller is operative to detect any air in the pressure chamber and to appropriately open the vent output valve to vent the air and to alarm should the condition persist. Since the air rises upwardly into the pressure chamber, the pumping chamber in normal operation is substantially free of air. When the pumping chamber is controllably exhausted, only the intended infusate is administered into the patent output port, thereby preventing the possibility of admitting air into the patient.

Individual ones of a plurality of valve plungers to be described are received in corresponding ones of the apertures 230, 232, 234 (FIG. 2B) that are reciprocally moveable to push corresponding upstanding cylindrical projections 254 (FIG. 2D) into sealing contact with the apertures 206, 214, 216 to control the state of actuation of the corresponding fluid valves. The cylindrical projections with their associated plunger withdrawn flex out of contact with the corresponding apertures to allow fluid flow into and out of the pumping chamber 208. A pumping piston to be described is received in the pumping piston receiving aperture 240 (FIG. 2B). The piston is reciprocally moveable to controllably push the dome 256 (FIG. 2C) into the pumping chamber 208 as can best be seen in FIG. 2E. The fluid that accumulates therein during each pumping sequence to be described is thereby pumped through the patient output port and into the circulatory system of a patient. The rate of reciprocating motion of the pumping piston, its travel distance into the chamber 208, and the time interval between pumping strokes is selected to controllably administer intended volume of infusant in intended time intervals.

Figure 3:
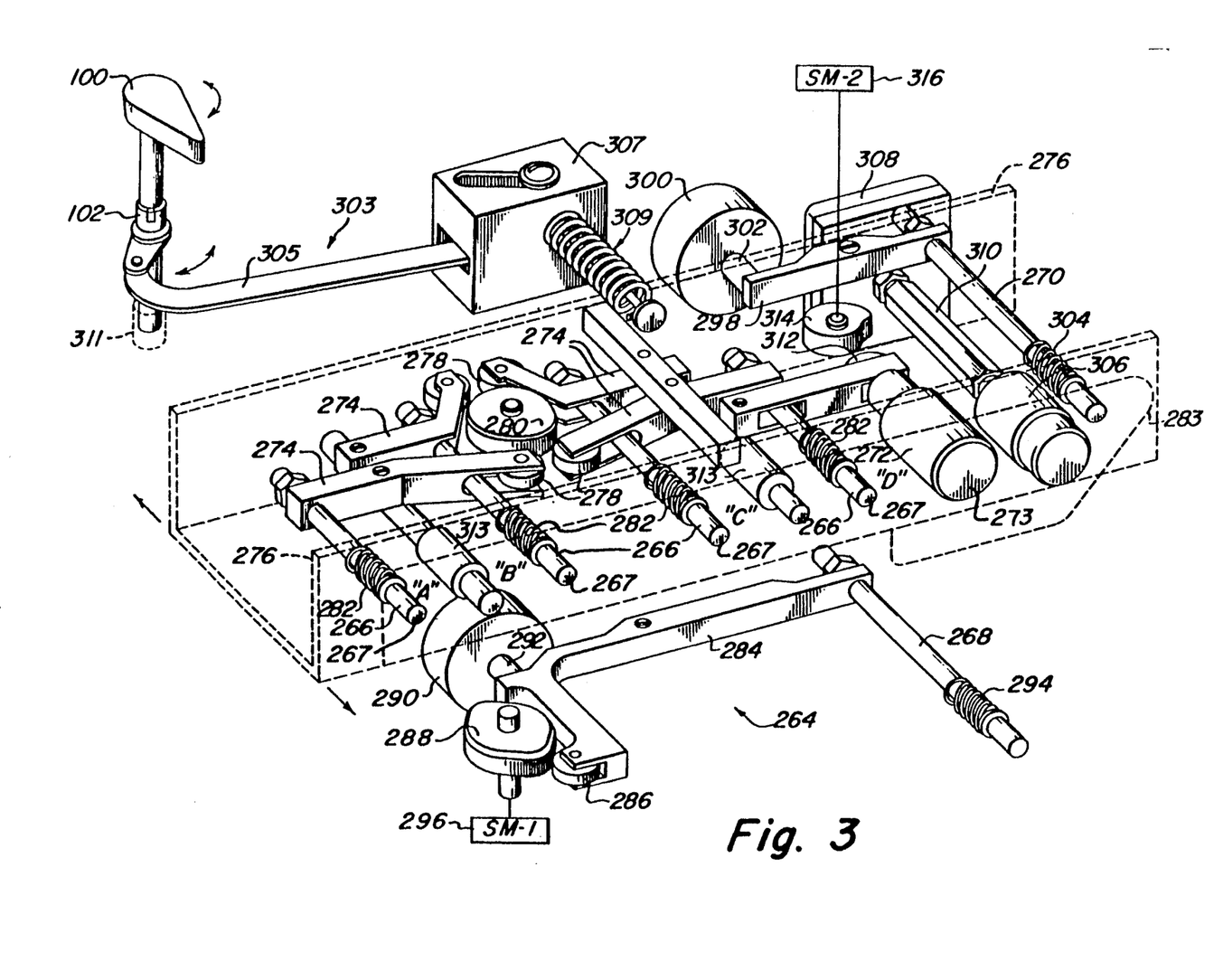
FIG. 3 is a partially exploded perspective view with the cover removed of a valve and pumping actuator of the infusion system of FIG. 1.

Referring now to FIG. 3, generally designated at 264 is a partially exploded perspective view with the cover removed of a valve and pumping actuator of the infusion system having plural fluid input ports and at least one patient output port according to the present invention. The assembly 264 includes a plurality of fluid input port valve plungers 266 each coaxially aligned with a corresponding one of the fluid input apertures 230 (FIG. 2D), an output valve port plunger 268 coaxially aligned with the output port aperture 232 (FIG. 2B), a vent valve port plunger 270 coaxially aligned with the collection bag aperture 234 (FIG. 2B), and a pumping chamber piston 272 coaxially aligned with the pumping chamber aperture 240 (FIG. 2E).

Each of the fluid input valve plungers 266 is slideably mounted in and fastened to a corresponding one of a plurality of rocker arms 274 that are individually pivotally mounted to a U-shaped support illustrated dashed at 276. A roller 278 is fastened to an end of each of the rocker arms 274. A cam 280 moving one lobe drives any selected one of the rollers 278 to withdraw the corresponding fluid input plunger 266 out of the corresponding ones of the fluid input port apertures. A compression spring 282 is slideably mounted on and fastened to corresponding ones of the plurality of fluid valve input plungers 266. The springs 282 act against one wall of the U-shaped support 276 urging the plungers 266 into corresponding ones of the fluid input ports designated "A", "B", "C", "D" of a cassette schematically illustrated at 283 to maintain the corresponding valves in a normally closed condition.

The output valve plunger 268 is slideably mounted in and fastened to one end of a rocker arm 284 that is pivotally mounted to the support 276. A roller 286 is fastened to an end of the rocker arm 284 remote from the end in which the plunger 268 is mounted. A cam 288, having two lobes 180° apart, coaxial with the cam 280, drives the roller 286 to withdraw the output valve plunger 268 out of the output valve aperture. A solenoid 290 having a displaceable ram 292 is fastened to the support 276 with its ram 292 in contact with the end of the rocker arm 284 remote from the plunger 268. The ram 292 is selectably actuable to withdraw the output valve plunger 268 out of the output valve aperture. A spring 294 is slideably mounted on and fastened to a plunger 268. The spring 294 acts against the one wall of the U-shaped support 276 urging the plunger 268 into the output port aperture for biasing the output valve in a normally closed condition. The cam 280 and the coaxial cam 288 are mounted for rotation with the shaft of a stepper motor 296. The system controller controllably rotates the stepper motor 296 to selectively actuate the input and output valves to implement a desired pumping sequence as appears more fully below. The lobes on the cams 280, 288 are so arranged as to prevent any input port and the output port from being simultaneously in an open condition for any rotary position of the stepper motor 296 to prevent unintended gravity flow infusion. Whenever it is desired to simultaneously open any input port and the output port such as during priming, the system controller rotates the stepper motor 296 to the position that opens the selected input port and actuates the solenoid 290 to open the output port.

The vent plunger 270 is slideably mounted in and fastened to a rocker arm 298 that is pivotally mounted to the U-shaped support 276. A solenoid 300 having a displaceable ram 302 is fastened to the support with its ram 302 in contact with the rocker arm 298. The ram 302 is selectably actuable to withdraw the vent output valve plunger 270 out of the collection bag output aperture to open the vent valve. A spring 304 is slideably mounted on and fastened to the vent plunger 270. The spring 304 acts against one wall of the U-shaped support 276 urging the plunger 270 into the collection bag port to maintain the vent valve in a normally closed condition.

A pressure head 306 fastened to a pressure transducer 308 via a longitudinally adjustable mechanical linkage 310 is coaxially aligned with the pressure chamber. The pressure head 306 includes an internal coaxial rod, not shown, positioned over the aperture 220 (FIG. 2A) that is displaced in a direction along its length in response to pressure variations in the pressure chamber 212 (FIG. 2A). The pressure transducer 308 converts the linear movement into an analog signal proportional to pressure in the pressure chamber.

A roller 312 is fastened to the end of the pumping piston 272 that is remote from the end that enters the pumping chamber 208 (FIG. 2A). A cam 314 having a spiral shaped bearing surface mounted for rotation with the shaft of a stepper motor 316 selectively drives the roller 312 for controllably displacing the pumping piston 272 for reciprocating motion into and out of the pumping chamber 208 (FIG. 2A). The support 276 is mounted in the housing for sliding motion by a mechanical linkage generally designated 303 connected between the lever 100 and the support 276. The linkage 303 includes a rod 305 pivotally mounted on one end to the lever 100 and connected on its other end to a member 307. A spring biased rod generally designated 309 is connected to one end to the support 276 and on its other end to a cam, not shown, interiorly of the member 307. A microswitch 311 is provided for sensing the axial position of the lever 100. Lifting the lever 100 axially out of the safety mechanism 102 and rotating it either clockwise or counterclockwise displaces the member 307 thereby urging the rod 309 toward and away from the support 276 for moving the support 276 and therewith the plungers and pistons into and out of the associated apertures provided therefor on the cassette. The switch 311 senses the axial position of the lever 100 to provide an indication of whether or not the cassette is locked in place. Extending alignment rods 313 are provided that cooperate with associated apertures provided therefor on the cassette, not shown, to help align the cassette in its intended operating position.

Figure 4:
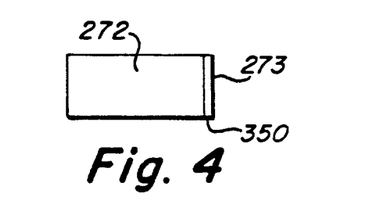
FIG. 4 is a side view of a pumping piston of the infusion system according to the present invention.

In the preferred embodiment of the present invention, the pumping piston 272 has a face 273 which presses against the dome 256 on the diaphragm 198 as the pumping piston 272 enters the aperture 240 of the pumping chamber 208. As best seen in FIG. 4, the face 273 comprises a cover 350 formed of a material similar to the material used to form the diaphragm dome 256. The materials must be similar such that there is no exchange of free electrons in the outer energy levels of the atoms comprising each material. Preferably, the identical material is used for both the piston face and the diaphragm.

Preferably, silicon rubber is used as both the diaphragm and the piston face, although the particular material used is not critical to the operation of the present invention, as long as it is similar on both the piston face and the diaphragm. A further embodiment contemplates forming the entire piston 272 from the same material.

The input port valve plungers 266 each has a face 267 which presses against the cylindrical projections 254 of the diaphragm 198. These faces 267 may also be formed from a material similar to that of the diaphragm 198. Alternatively, the entire plunger 266 may be formed of the same material.

Figure 5:
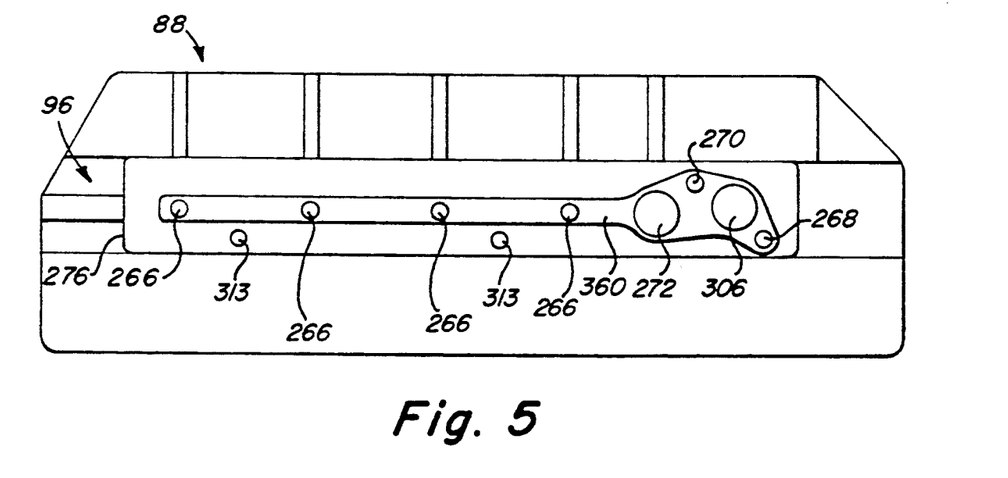
FIG. 5 is a side view of the housing of the infusion system with the cassette removed according to an alternative embodiment of the present invention.

FIG. 5 shows a further embodiment of the housing 88 showing the channel 96 with the cassette removed. In the prior art pumping system, support 276 or the walls of the channel 96 are formed of a metal and the cassette is formed of an acrylic. When the cassette is slid into place, the relative motion between these dissimilar materials generates electric charges. In the present invention, an insert 360 is provided on support 276 to align with the fluid flow path in the cassette. This insert 360 is formed of the same material as the cassette, preferably acrylic. This insert reduces the amount of charge induced near the flow path when the cassette is slid into the channel 96 of the housing 88. The insert 360 may also be wider than shown in FIG. 5 to cover a greater area.

In an alternative embodiment, the cassette may be covered with a material similar to that used in the channel 96 or support 276. If the channel or support is formed of a metal, the cassette may be covered with a metal foil. The cover may extend over the entire area of the cassette or just over a portion of the cassette such as along the fluid flow path.

In a further embodiment, the cassette may be coated with an antistatic material. For example, the cassette may be sprayed with an antistatic spray.

Figure 6:
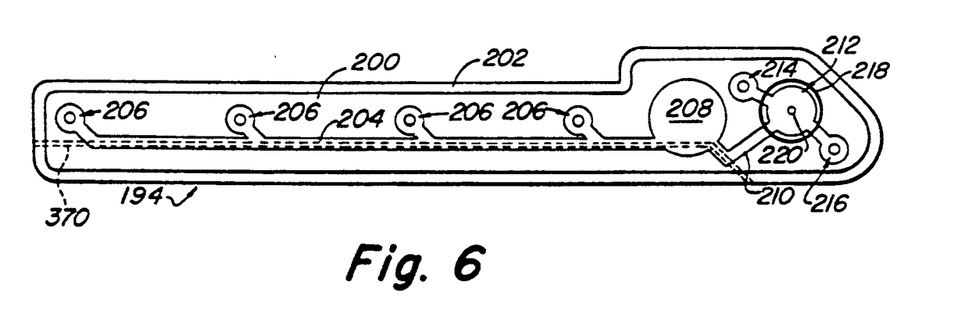
FIG. 6 is a plan view of one portion of the cassette of the infusion system according to a further embodiment of the present invention.

A further embodiment is shown in FIG. 6. A ground wire 370 is embedded in the first housing portion 194. The ground wire is aligned with the fluid flow channel 204. A suitable connection to ground is provided on the housing 88 to which the wire 370 is connected. In this manner, any electrical currents generated by induced electric charges are carried to ground, rather than down to the patient in the fluid.

It will be appreciated that, while the invention has been described in relation to an infusion pumping system as disclosed in U.S. Pat. No. 4,696,671 to Epstein, the invention can be applied to any infusion pumping system. For example, in a peristaltic type of pumping system, the rollers or other members which squeeze the tubing and the tubing itself may be formed of a similar material.

It will be appreciated that many modifications of the presently disclosed invention will be apparent to those skilled in the art without departing from the scope of the appended claims.

We claim:

1. An infusion system for administering infusates to a patient comprising:
    a pumping system including means for pumping the infusates from at least one fluid flow line to at least one fluid outlet flow line connected to the patient; and
    means associated with an interface between the pumping means and the infusate for preventing static electricity from causing artifact in an electrocardiogram of the patient.

2. The infusion system of claim 1 wherein the artifact preventing means comprises means for preventing the generation of static electricity at the pumping means.

3. The infusion system of claim 2 wherein the pumping means further includes a pumping chamber, a flexible diaphragm forming a wall of the pumping chamber, and a pumping piston mounted for reciprocal movement into and out of the pumping chamber, the pumping piston having a face disposed to push against the diaphragm; and the static electricity preventing means comprises forming both the face of the piston and the diaphragm from a material tending to reduce the exchange of electrical charge between the piston face and the diaphragm.

4. The infusion system of claim 3 wherein the pumping means further includes an inlet valve comprising a valve aperture, a valve diaphragm, and a valve piston mounted for reciprocal movement into and out of the valve aperture and having a face disposed to push against the valve diaphragm to close the valve aperture; and the static electricity preventing means further comprises forming the inlet valve piston face and the inlet valve diaphragm from a further material tending to reduce the exchange of electrical charge between the inlet valve piston face and the inlet valve diaphragm.

5. The infusion system of claim 2 wherein:

the pumping means further comprises:

a housing having cassette receiving means, a cassette releasably mounted to the cassette receiving means of the housing, the cassette including means for receiving the at least one fluid inlet flow line and means for receiving the at least one fluid outlet flow line; and the artifact preventing means comprises the cassette and the cassette receiving means being comprised of a material tending to reduce the exchange of electrical charge at all points of contact.

6. The infusion system of claim 2 wherein:

the pumping means further comprises:

a housing having cassette receiving means, and a cassette releasably mounted to the cassette receiving means of the housing, the cassette including means for receiving the at least one fluid outlet flow line; and the artifact preventing means comprises a coating of antistatic material on the cassette.

7. The infusion system of claim 6 wherein the antistatic coating is sprayed on the cassette before the cassette is mounted in the cassette receiving means of the housing.

8. The infusion system of claim 11 wherein the artifact preventing means comprises means for preventing a flow of electric current down the at least one fluid outlet flow line to the patient.

9. The infusion system of claim 8 wherein the current preventing means comprises means for electrically grounding a static electricity-induced electric current generated at the pumping means.

10. The infusion system of claim 9 wherein the pumping system further includes an electrical connection to a ground, the pumping means includes a fluid flow line, and the grounding means comprises an electrical conductor disposed along a portion of the fluid flow line to be in electrical contact with infusates flowing along the fluid flow line and further connected to the electrical connection to the ground.

11. The infusion system of claim 10 wherein the electrical conductor is an electrically conductive wire.

12. The infusion system of claim 1 wherein the pumping means further includes a pumping chamber, a flexible diaphragm forming a wall of the pumping chamber, and a pumping piston mounted for reciprocal movement into and out of the pumping chamber, the pumping piston having a face disposed to push against the diaphragm, and the artifact preventing means comprises the face of the piston and the diaphragm each being formed from a material tending to reduce the exchange of electrical charge between the piston face and the diaphragm.

13. The infusion system of claim 12 wherein the material forming the piston face and the diaphragm is silicon rubber.

14. The infusion system of claim 12 wherein the pumping piston is formed entirely of the material of the piston face.

15. The infusion system of claim 12 wherein the pumping means further includes an inlet valve comprising a valve aperture, a valve diaphragm, and a valve piston mounted for reciprocal movement into and out of the valve aperture and having a face disposed to push against the valve diaphragm to close the valve aperture, wherein the inlet valve piston face and the inlet valve diaphragm are both formed of a further material.

16. The infusion system of claim 15 wherein the further material is silicon rubber.

17. The infusion system of claim 1 wherein the artifact preventing means comprises means for electrically grounding a static electricity-induced current generated at the pumping means.

18. The infusion system of claim 17 wherein the pumping system further includes an electrical connection to a ground, the pumping means includes a fluid flow line, and the grounding means comprises an electrical conductor disposed along a portion of the fluid flow line to be in electrical contact with infusates flowing along the fluid flow line and further connected to the electrical connection to the ground.

19. The infusion system of claim 18 wherein the electrical conductor is an electrically conductive wire.

20. The infusion system of claim 1 wherein the artifact preventing means comprises means for dissipating a static electricity-induced charge generated at the pumping means.

21. The infusion system of claim 1 wherein the artifact preventing means comprises forming parts of the pumping means capable of relative motion to each other of a material tending to reduce the exchange of electrical charge.

22. An infusion system for administering infusates to a patient comprising:

a pumping system including means for pumping the infusates from at least one fluid inlet flow line to at least one fluid outlet flow line connected to the patient, the pumping means further including a pumping chamber, a flexible diaphragm forming a wall of the pumping chamber, and a pumping piston mounted for reciprocal movement into and out of the pumping chamber, the pumping piston having a face disposed to push against the diaphragm; and means associated with the pumping system for preventing the generation of static electricity at the pumping system comprising forming the face of the piston and the diaphragm from an identical material.

23. The infusion system of claim 22 wherein the pumping means further includes an inlet valve comprising a valve aperture, a valve diaphragm, and a valve piston mounted for reciprocal movement into and out of the valve aperture and having a face disposed to push against the valve diaphragm to close the valve aperture; and the static electricity preventing means further comprises forming the inlet valve piston face and the inlet valve diaphragm from a further identical material.

24. An infusion system for administering infusates to a patient comprising:
- a pumping system including means for pumping the infusates from at least one fluid inlet flow line to at least one fluid outlet flow line connected to the patient, the pumping means further comprising a housing having cassette receiving means, a cassette releasably mounted to the cassette receiving means of the housing, the cassette including means for receiving the at least one fluid inlet flow line and means for receiving the at least one fluid outlet flow line; and
- means associated with the pumping system for preventing the generation of static electricity at the pumping system, the static electricity preventing means comprising forming the cassette and the cassette receiving means of an identical material at all points of contact.

25. An infusion system for administering infusates to a patient comprising:
- a pumping system including means for pumping the infusates from at least one fluid inlet flow line to at least one fluid outlet flow line connected to the patient, the pumping means further comprising a housing having cassette receiving means, and a cassette releasably mounted to the cassette receiving means of the housing, the cassette including means for receiving the at least one fluid inlet flow line and means for receiving the at least one fluid outlet flow line; and
- means associated with the pumping system for preventing the generation of static electricity at the pumping system, the static electricity preventing means comprising a coating of antistatic material on the cassette.

26. The infusion system of claim 25 wherein the antistatic coating is sprayed on the cassette before the cassette is mounted in the cassette receiving means of the housing.

27. An infusion pumping system for administering infusates to a patient comprising:
- a pumping chamber;
- a diaphragm forming a wall of the pumping chamber;
- means for connecting a fluid inlet line to the pumping chamber;
- means for connecting a fluid outlet line to the pumping chamber; and
- a pumping piston mounted for reciprocal movement into and out of the pumping chamber, the piston having a face disposed to push against the diaphragm, wherein the piston face and the diaphragm are each formed of a material tending to reduce the exchange of electrical charge between the piston face and the diaphragm.

28. The infusion system of claim 27, wherein the fluid inlet line connecting means further comprises an inlet valve comprising a valve aperture, a valve diaphragm, and a valve piston mounted for reciprocal movement into and out of the valve aperture and having a face disposed to push against the valve diaphragm to close the valve aperture, wherein the inlet valve piston face and the inlet valve diaphragm are each formed of a further material tending to reduce the exchange of electrical charge between the piston face and the diaphragm.

29. An infusion pumping system for administering infusates to a patient comprising:
- a housing having an electrical connection to a ground and having disposable cassette receiving means;
- a disposable cassette releasably mounted to the cassette receiving means of the housing;
- the disposable cassette including means for receiving an inlet infusion flow line, means for receiving an outlet infusion flow line, and a fluid flow path connecting the inlet flow line receiving means to the outlet flow line receiving means;
- means for pumping along the fluid flow path from the inlet flow line receiving means to the outlet flow line receiving means; and
- means for electrically grounding the cassette to the electrical connection of the housing to the ground.

30. The infusion pumping system of claim 29, wherein the cassette grounding means comprises an electrical conductor attached to the cassette along a portion of the fluid flow path to be in electrical contact with infusates flowing along the fluid flow path, the electrical conductor further connected to the electrical connection to the ground.

31. An infusion pumping system for administering infusates to a patient comprising:
- a housing having cassette receiving means;
- a cassette releasably mounted to the cassette receiving means of the housing, the cassette including means for receiving at least one inlet infusion flow line and means for receiving at least one outlet infusion flow line;
- means for pumping infusates through the cassette from the inlet flow line receiving means to the outlet flow line receiving means; and
- the cassette and the cassette receiving means each being comprised of a material tending to reduce the exchange of electrical charge at all points of contact.

* * * * *